United States Patent [19]

Silverman et al.

[11] Patent Number: 4,709,265
[45] Date of Patent: Nov. 24, 1987

[54] REMOTE CONTROL MOBILE SURVEILLANCE SYSTEM

[75] Inventors: Eugene B. Silverman, Ellicott City; Richard K. Simmons; Robert B. Croston, both of Columbia, all of Md.

[73] Assignee: Advanced Resource Development Corporation, Columbia, Md.

[21] Appl. No.: 787,338

[22] Filed: Oct. 15, 1985

[51] Int. Cl.$^4$ .................. H04N 7/10; H04N 13/00; H04N 5/30
[52] U.S. Cl. ................................... 358/108; 358/87; 358/88; 358/210; 358/229; 73/863; 73/864.71; 901/1
[58] Field of Search ............... 358/87, 88, 100, 108, 358/210, 229; 89/41.05, 41.01, 41.09; 340/723, 724, 725; 355/47; 364/522; 354/94, 95; 73/863, 863.33, 864, 864.71; 901/1, 14, 44; 414/729

[56] References Cited

U.S. PATENT DOCUMENTS 3,430,496 3/1969 Swanberg et al. ................. 73/864.7
4,483,407 11/1984 Iwamoto et al. ........................ 901/1
4,549,208 10/1985 Kamejima et al. ................. 358/108

OTHER PUBLICATIONS

E. B. Silverman, "Robotic Technology Experiments for Nuclear Power Plant Inspection and Maintenance" (1982), pp. 109–112 ANS Reprint.
Gupton, "Nuclear Power Plant Emergency Damage Control Robot", Robotic Age, pp. 18–21 (Mar./Apr. 1983).
Kohler, "Ferngelenktes Manipulator—Fahrzeug MF3", VDI-Z 120 No. 22 (Nov. 1978).

Primary Examiner—Howard W. Britton
Assistant Examiner—John K. Peng
Attorney, Agent, or Firm—Sughrue, Mion, Zinn, Macpeak and Seas

[57] ABSTRACT

A surveillance system for hazardous environments and the like having a radio remote controlled vehicle that is sized and shaped for optimum maneuverability and stability, including mobility on stairs and inclined surfaces. The vehicle is designed to have a low center of gravity that is shiftable up and down, front to rear and side to side under operator control in order to provide stability. The top deck of the vehicle is uniquely shaped and is adapted to support any of several payloads, including an articulated arm module that is moveable in a pan and tilt direction and a smear sampler mechanism for repeatedly taking surface samples. The vehicle is moved by independently operated, motor driven tracks located on each of the two longitudinal sides of the vehicle and is adapted to move in a forward, reverse and rotational directions. Remote monitoring is provided by stereoptic TV cameras, stereo sound, and variety of environmental sensors.

14 Claims, 22 Drawing Figures

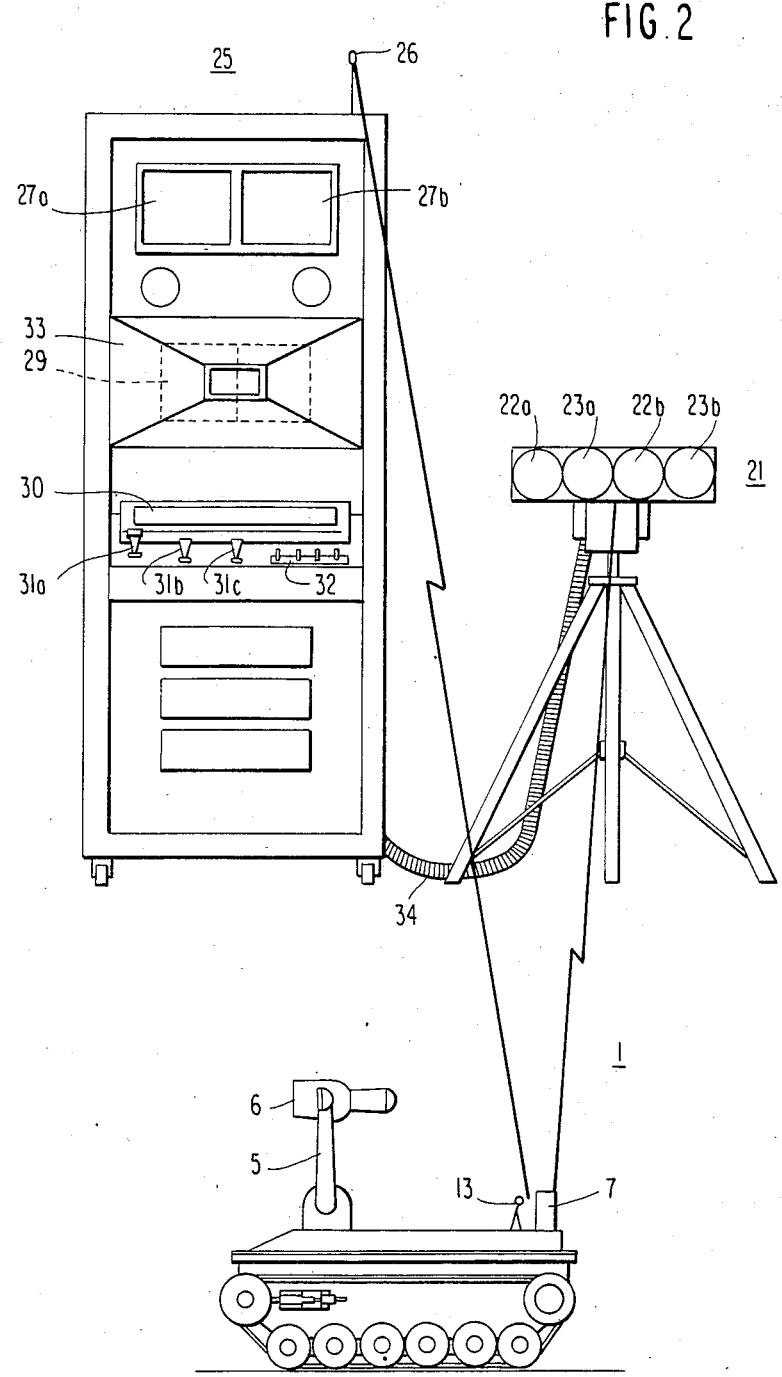

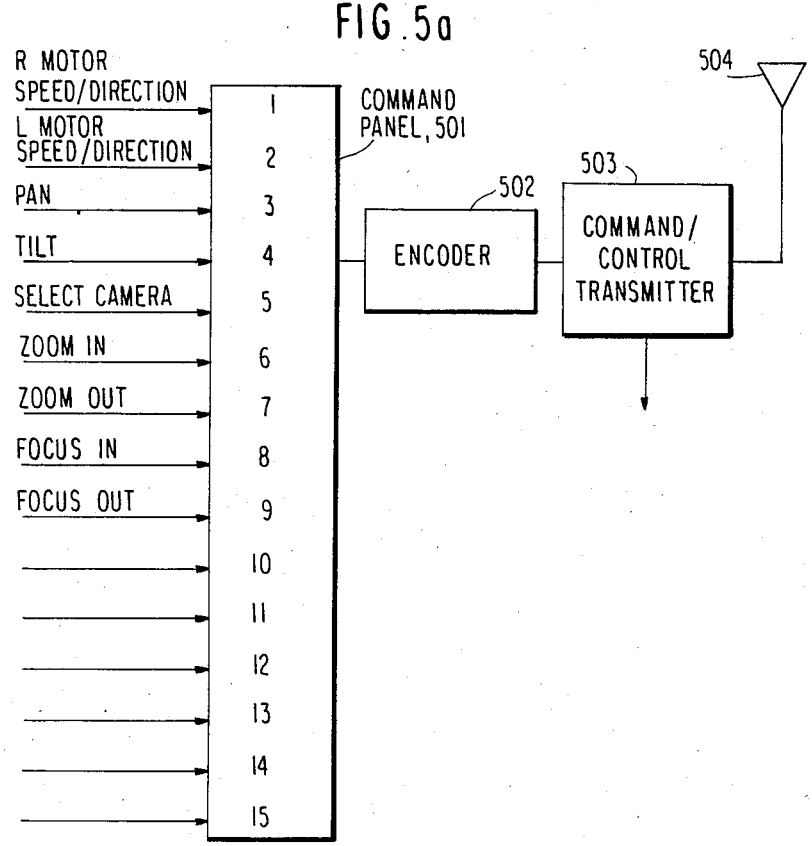
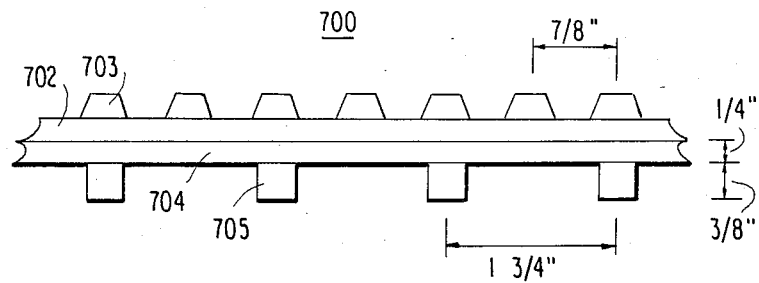
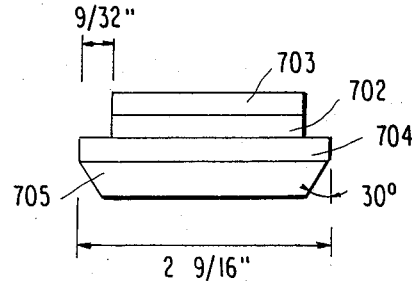

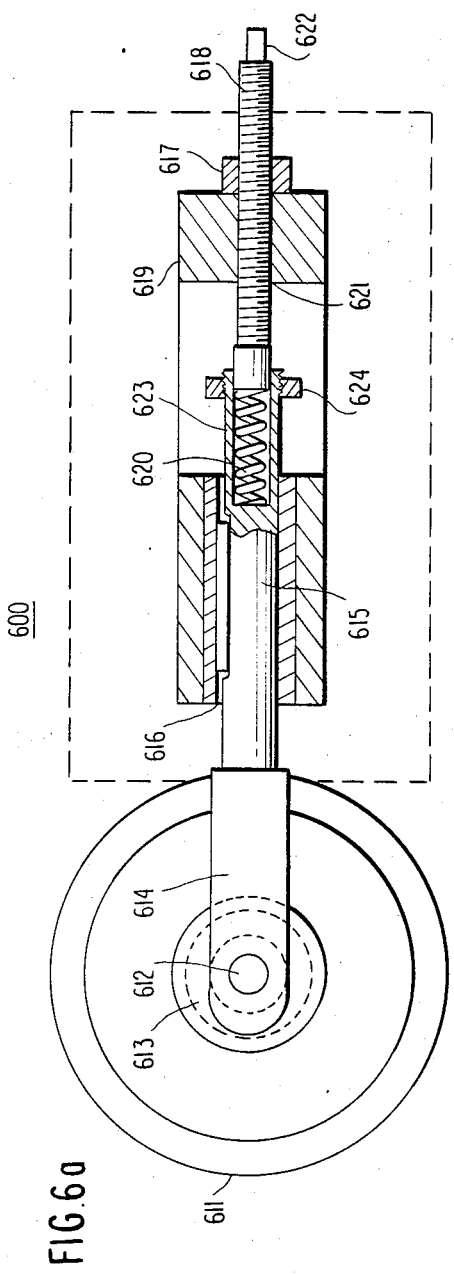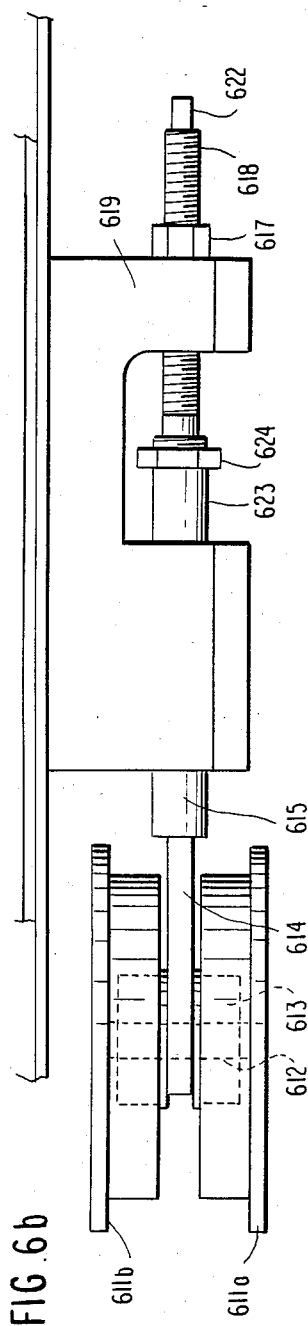
FIG.6a
FIG.6b

FIG. 9a
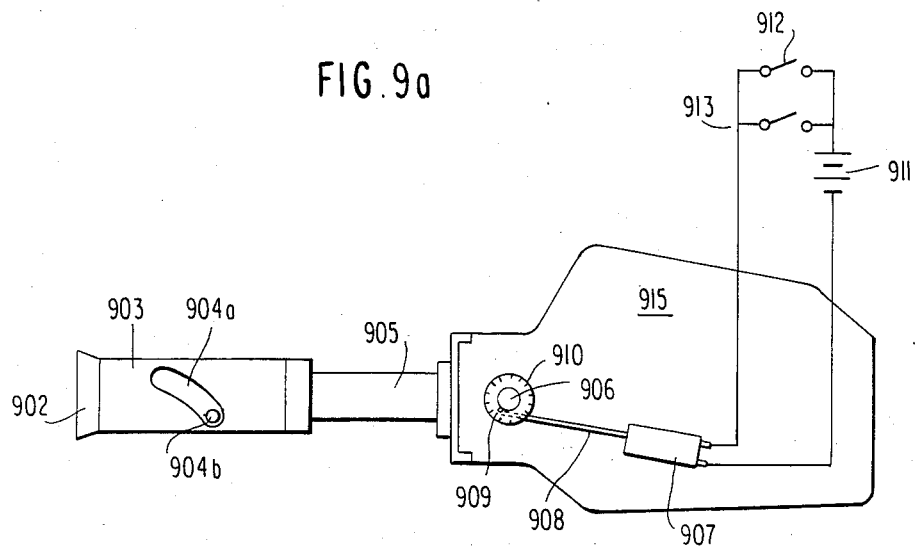
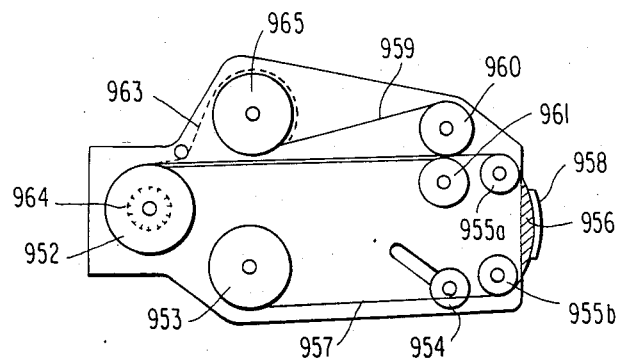
FIG. 9b

REMOTE CONTROL MOBILE SURVEILLANCE SYSTEM

BACKGROUND OF THE INVENTION

The present invention relates to a surveillance system having a remotely controlled vehicle for use in hazardous environments, such as nuclear power facilities and toxic chemical manufacturing operations, the vehicle being adapted to monitor a wide variety of environmental conditions and to have optimum mobility throughout a facility.

The environmental dangers related to nuclear power plants, hazardous chemical production and storage facilities, hazardous waste storage areas and industrial spills, are well known. Often, the solution to environmentally hazardous problems requires both an initial analysis and continued monitoring of the environment, including the operational condition of machinery, valves, gauges and the like, without the exposure of personnel to the related environmental dangers. It also is desirable to have the capability to take multiple samples from the wall, floor and equipment surfaces of a contaminated facility. Subsequent corrective action must be taken to solve the underlying problem. The use of a remotely controlled robot to examine a damaged nuclear power plant and to take corrective action to repair damage which may have been caused to the plant facility is shown in the publication entitled "Nuclear Power Plant Emergency Damage Control Robot", Gupton, *Robotic Age*, pages 18-21 (March/April 1983). The proposed vehicle has motors, lights, electronic equipment, a communications capability, which also include video transmission capabilities, and batteries for operation remote from a source of high power. However, this and similar prior art systems teach the use of large, heavy and complex mobile vehicles which normally are tethered to a central control facility by a cable that provides both power and a communications/control capability. These vehicles are very expensive and their broad range of capabilities requires a substantial structure weighing several tons and having significant power requirements. Moreover, such vehicles often are limited to predetermined paths and lack the mobility required in multilevel facilities as well as the maneuverability required to move through tight passages, under equipment and around barriers. Notwithstanding their substantial cost, they have significant limitations that prevent them from being cost effective. A more manageable, remotely-controlled robot system in shown in the publication, "Ferngelenktes Manipulator—Fahrzeug MF3", Kohler, *VDI-Z* 120 No. 22 (November 1978). There, a tethered, remotely-controlled robot is configured to have four independently operating drive track mechanisms each of which supports one corner of a rectangular payload platform. Each drive mechanism comprises a continuous tread belt which is wrapped around a drive sprocket, driving wheels and tensioner wheel. The payload platform is equipped with one or two articulated manipulator arms that can be adapted to perform a variety of complex end-effect functions, including holding, lifting, welding and drilling. The payload platform also contains lights and a pair of television cameras which are adapted to provide a stereo-optic view capability to a remote control station. At the control station, an operator may use the stereo-optic viewer and a "joystick" control to operate the device. The robot is sized to move through doorways and has a stair-climbing capability which enables it to move about a multilevel facility; however, the vehicle cannot negotiate stairways with small landings. This and similar structures taught in the prior art continue to be complex, weighing a substantial amount and having a weight and length which restricts their maneuverability. Moreover, the prior art teaches mobile vehicles that are tethered by power and telecommunications cables, which provide a further restriction on their maneuverability and the danger of snagging, particularly when moving to another level in a multilevel facility. Additionally, no prior art structure has the capability of obtaining samples from various surfaces within a facility on a repetitive basis, other than through the grabbing capability of an articulated arm with clamping extremities. Finally, all of the prior art devices are complex and, necessarily expensive to manufacture and maintain.

In order to solve the problems confronted by the prior art, the present invention teaches a surveillance system having a unique remotely controlled vehicle. The vehicle is designed with a modular structure, is adapted to perform the necessary surveillance functions and is sized to provide optimum manueverability and stability. A uniquely shaped chassis is sized to move easily through standard doorways, standard stairways, and narrow passages while having a length sufficient to provide both stability on inclined surfaces and maneuverability in confined spaces, such as landings. The vehicle is relatively lightweight and the chassis is designed to accommodate most of the weight at the lowest possible point in the body in order to provide an optimally low center of gravity which is displaced slightly forward of the center of the vehicle. The top deck of the vehicle is uniquely shaped and adapted to support any of several payloads mounted at a point forward to center of the vehicle. One such payload is an articulated arm module which comprises a turret containing an articulated arm capable of moving in pan and tilt and having a load affixed to its end which may provide visual, sampling or other sensing capabilities. The top cover, which is adapted to fit over the top of the chassis, slopes down toward the front and sides of the vehicle in order to permit a deployment of the payload in a manner that will augment the vehicle's climbing capabilities by further shifting the center of gravity to an optimum position. An independently-operated, motor-driven track is located on each of the two longitudinal sides of the vehicle; the tracks are adapted to provide motion in a forward, reverse and rotational direction. The tread is supported by wheels spaced along the bottom of the chassis and is driven by a motor controlled sprocket. A tensioner sprocket is used to provide the proper amount of flexibility to the tread for optimum traction over various types of surfaces. The tread itself is adapted to have maximum traction and is shaped to avoid being wedged in standard industrial surfaces such as drain grates and metal stairways.

The vehicle is adapted to have a plurality of payloads and payload mounts which provide flexibility in a wide variety of industrial applications. A standard payload includes a rotatable turret mounted on the vehicle deck and having an articulated arm for moving through a horizontal to a vertical direction. The arm is adapted to contain various loads, including television cameras, smear samplers and the like.

An object of the present invention is provision of a lightweight, maneuverable and optimally sized remote control vehicle for sensing the ambient conditions in hazardous environments.

A further object of the invention is to provide a remotely controlled vehicle which is free of power, telecommunications, command or control cabling.

Another object of the invention is the provision of remote control vehicle having on a top cover, a rotatable turret with an articulated arm and a useful payload at the end thereof and which is also adapted to be moved below the horizontal plane at which the turret joins the top cover, in order to provide a capability of shifting the center of gravity.

A further object of the invention is the provision of a remotely controlled vehicle having the capability of taking multiple smear samples from the surfaces of a hazardous environment facility.

Yet another object is the provision of a remotely controlled vehicle which is inexpensive to manufacture, easy to control and requires a minimum of maintenance and adjustment.

Another object of the invention is to provide a remotely controlled vehicle, having two parallel and independently driven track mechanisms, each disposed along the longitudinal sides and attached to run between the front and back of the vehicle, which is adapted to climb conventional stairways.

SUMMARY OF THE INVENTION

The present invention comprises a remotely operated, battery powered, tracked, tetherless vehicle that is adapted to carry multiple payloads, including optics, sensors, smear samplers, articulated or telescoping arms and related control electronics. The invention has a unique size and shape which permits optimal distribution of the center of gravity for climbing conventional stair cases in industrial facilities. The payload packages carrried by the vehicles are adapted to rotate about a vertical vehicle axis. A further embodiment of the invention includes a payload incorporating a novel yoke design which is used to provide pan and tilt motion to all payloads (articulated arms, telescoping arms, cameras, sensors, etc.).

BRIEF DESCRIPTION OF THE DRAWINGS

FIG. 2 shows a preferred embodiment of the system for remotely controlling the vehicle.

FIGS. 5A and 5C are block diagrams of the control station electronic subsystem.

FIGS. 6A and 6B are illustrated of a preferred tread tensioner design.

FIG. 7A is an illustration of a preferred tread design.

FIG. 7B is a cross section of the tread design of FIG. 7A.

FIG. 9A shows the schematic of a smear sampler holder.

FIG. 9B shows the schematic of a smear sampler cassette.

DESCRIPTION OF THE PREFERRED EMBODIMENTS

Figure 1A:
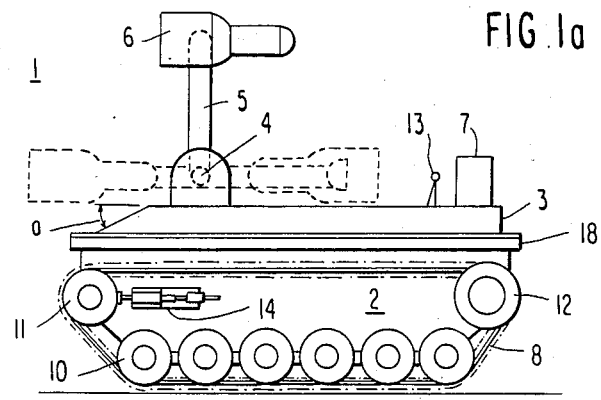
FIGS. 1A, 1B, and 1C show a preferred embodiment of the invention having various payloads, including single inspection camera, smear sampler and basic tilted yoke mechanism.

Referring to FIG. 1A, a remote control vehicle 1 is shown having a base chassis 2 and a top cover 3. Propulsion is provided by a combination of motors, drive wheels, belt-type tracks and related tensioner mechanisms. In particular, the chassis contains six road wheels 10 per side which are mounted to the chassis 2 by stub shafts that are threaded into the chassis. A drive wheel 12 is located on each side panel of chassis 2 in the upper rear portion of the side panel. An idler wheel 11 and tensioner mechanism 14 are located at the front portion of each side panel of the chassis 2. A continuous belt-like track 8, having a unique tread design, is adapted to wrap around the drive wheel 12, the road wheels 10 and the tensioner wheel 11 on each side of chassis 2. The chassis is affixed with a top cover 3 on which are mounted one or more television transmitting antennas 13, a command receive antenna 7 and a payload, which in FIG. 1A is a turret 4, having an articulated arm 5 and camera 6 mounted at the end of the arm. As shown in FIG. 1A, the cover is substantially horizontal with a front apron portion, shown as 3a in FIG. 1B, falling from the horizontal plane at an angle a, where a is approximately 25 degrees in a preferred embodiment. The angle a may be chosen in a range of 20 to 35 degrees. A bumper guard 18 is made of rubber or other shock absorbent material and is fixed around the top perimeter of the chassis 2 and provides a shock absorbing capability should the vehicle strike other objects.

Figure 1B:
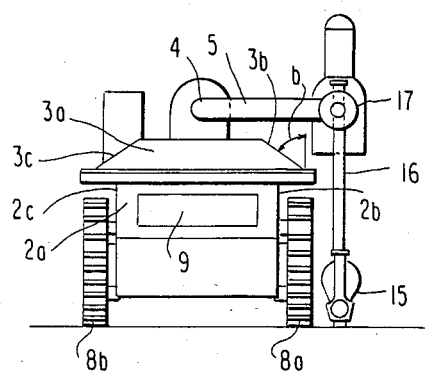

Referring to FIG. 1B, a front view of the vehicle 1 is shown. The chassis 2 has a front side 2a in which a window 9 is located for viewing by a stereo-optic system, as will be described later. On each of the longitudinal sides of the chassis 2b and 2c, identical drive tracks 8a and 8b are shown. The top cover at each side of the vehicle can be seen to have two sloping portions 3b and 3c, each of which varies from the vertical by an angle b, where b is approximately 57 degrees in a preferred embodiment. The angle b may be chosen in a range of 40 to 55 degrees. FIG. 1B shows the articulating arm 5 rotated by the turret 4 to one side of the vehicle and illustrates a smear sample mechanism 15 attached to the tip of the arm 5 through a rotatable joint 17 and arm extender 16.

Figure 1C:
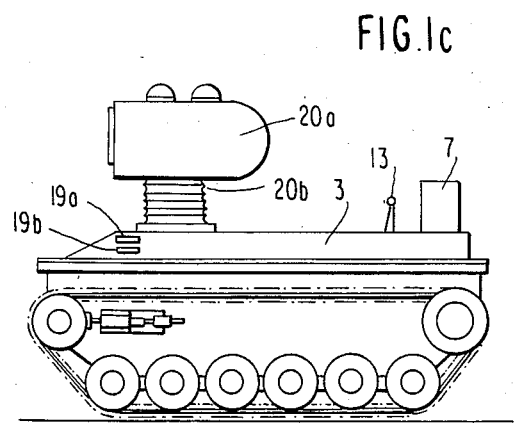
Figure 1D:
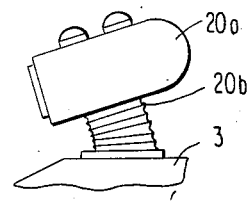
FIG. 1D shows the payload in FIG. 1C in a tilt position.

FIG. 1C illustrates the basic vehicle 1 with a stereo-optic zoom-lens camera payload 20a mounted on a panable and tiltable platform 20b. An illustration of the structure in the forward tilt position is shown in FIG. 1D. The details of this structure are provided below with respect to the discussion of FIG. 8B. A variety of environmental sensing devices (19a and 19b) such as temperature sensor, relative humidity sensors, radiation sensors, chemical sensors, and air quality monitors, may be mounted on the top cover 3 of the vehicle as shown and on the pan and tilt payload 20a. Sensor output is provided to a conventional telemetry communications systems located within the vehicle for transmission by antenna 7. Antenna 7 is an omnidirectional antenna but may be a rotating directional antenna, as is well known in the art.

FIG. 2 is an illustration of a remote control system for monitoring the environment with the mobile sensing vehicle. A supervisory control station 25, which is operator controlled through a keyboard 30, joysticks 31a, 31b and 31c as well as switch group 32, permits the operator to drive the vehicle, position it and operate the payload elements. Typically the control package can contain a four-position joystick that moves the vehicle inspection optics horizontally right and left (pan); moves the articulated arm backward and forward; rotates the inspection optics housing up and down. Vehicle movement is controlled by two-position proportional joysticks that control vehicle motors. Push sticks forward, the vehicle moves forward; pull sticks back, vehicle reverses; one stick forward, one back, the vehicle spins on its axis right or left. Vehicle speed depends on joystick displacement, forward or back, in a conventional manner. Two 3-position (normally off) switches provide surveillance camera control (inspection optics; zoom-in and zoom-out; focus-in and focus-out). The keyboard includes a two-position switch that provides main power shutoff. Additional miscellaneous functions may be provided by other control switches that may operate ancillary features of the remote vehicle 1 such as drive power on and off switches, smear sampler activation switches, etc. Additional joysticks may be added to perform such functions as: move a telescoping arm in and out; open and close a manipulation on the end of either the telescoping arm or in place of the smear sampler in a manner that is conventional and well known in the prior art. The keyboard 30 combined with a conventional microprocessor can provide similar or ancillary control functions.

A 3-D display 29 comprises two television monitors 40 and provides the operator with a three-dimensional view of the scene in front of the vehicle. Each monitor receives a TV signal from one of two TV cameras mounted within the body of the vehicle and aligned to view the scene through the transparent port 9, illustrated in FIG. 1B. The two scenes are optically merged into a single 3-D view by the 3-D hood 33. The operator may also command the display of television signals from a camera 6 mounted on the articulated arm 5 of the vehicle. The inspection camera 6 ca be pointed in any direction to inspect equipment, floors, and walls. The scene from this camera is displayed on monitor 27a. Environmental data, continuously generated by transducers 19A, 19B, etc., is transmitted by the vehicle communications system to the control station. When received, the telemetry is procesed and displayed to the operator on screen 27b. Environmental and vehicle status data is transmitted on the video side bands, formatted by a programmable minicomputer and displayed in a conventional manner as is well known in the prior art. Commands from control elements 30-32 are transmitted to the vehicle by antenna 26 over an RF link.

A telecommunications cable 34 is connected between the control center 25 and an antenna array 21. The array includes two pairs of antennae (22A and 22B), (23A and 23B) which are adapted to receive each of two TV channels redundantly. The antenna assembly may be implemented with a space diversity concept to minimize video signal interference from multipath and other interference with the signal that is broadcast from the vehicle. Two channels of video, with data and audio on the sidebands are each received by a pair of the four antennas seen in the Figure. The strongest signal for each channel may be selected with switching circuitry.

Figure 3:
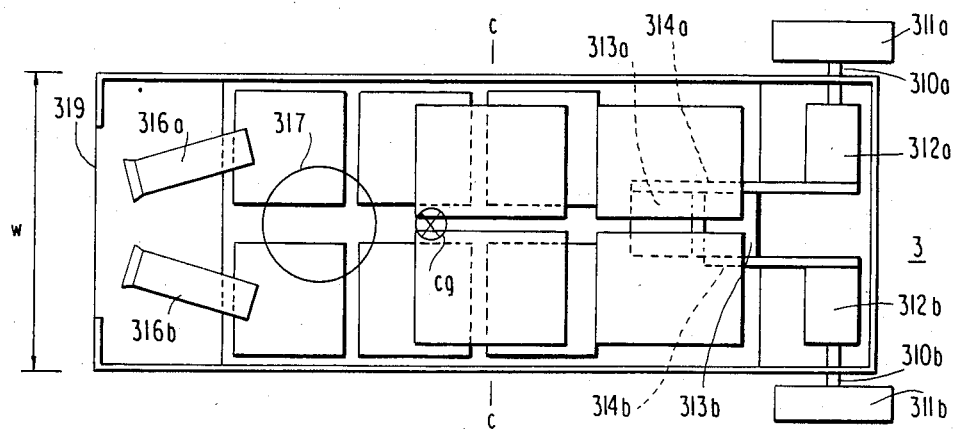
FIG. 3 shows the silhouette of the vehicle chassis from a top view, with the location of certain components illustrated therein.
Figure 4:
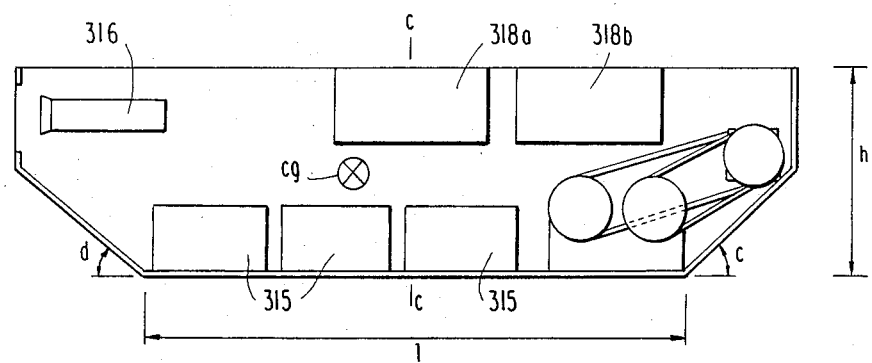
FIG. 4 shows the vehicle chassis from a side view.

Referring to FIG. 3, a top view of chassis 2 is shown to illustrate the placement of certain components. Toward the rear of the chassis 2 and on each side thereof is mounted a drive wheel 311a and 311b which are connected by drive shafts 310a and 310b to gear boxes 312a and 312b, respectively. Each gear box is connected to an individually controlled motor 313a and 313b through drive belts 314a and 314b, respectively. As seen in FIG. 4, the drive wheel 311 and gearbox 312 are mounted at the top rear of the chassis while the motors 313 are disposed at the lowest rear portion of the chassis. The lower rear portion of the chassis is angled upwards in order to provide the necessary clearances during stair climbing and descending operations. The optimum angle c, as shown in FIG. 4, would be in the range of 40 to 60 degrees; in other words the rear bow portion is angled upward from the bottom portion at an angle of 120°-140°. The height h of the chassis is made as small as possible and, given the load requirements for the vehicle, would be in the range of 10 to 12 inches. The length of the lower portion of the chassis, identified as 1, is optimally sized to span three conventional stairs and is typically 31 to 33 inches. The width of the vehicle, identified as w in FIG. 3 is typically 15.5 to 16.5 inches in order to provide maneuverability through doorways and within passageways suitable for travel by personnel. Substantially forward of the center of the vehicle and located along the bottom of the chassis are batteries 315. These batteries may be sealed, lead acid gel batteries which provide the required power for operating the vehicle and its communications system. The placement of the batteries at the lowest point in the chassis provide a low center of gravity which is essential for stair climbing stability. At the front of the vehicle, as illustrated in FIG. 4, the chassis rises at an angle d which is typically in a range of 40 to 60 degrees; in other words the front bow portion is angled upward from the bottom portion at an angle of 120°-140° to provide optimum stair and obstacle climbing capability. The stereo-optic viewing port 319 permits high resolution, television camera 316a and 316b, having auto zoom capability, to provide a three-dimensional view of the foreground environment for the vehicle. The cameras may have audio pickup microphones either built in or otherwise attached on opposite sides of the vehicle in order to provide a bidirectional sound localization capability. A center line, designated in FIGS. 3 and 4 as C—C may be used to locate the forward placement of the payload package 317. Telecommunications, management and control electronics are located in removable baskets 318a and 318 b. The distribution of weight within and above chassis 2 provides a center of gravity which is located in a point C-G, as illustrated in the FIGS. 3 and 4, which is optimally located forward of the center line and low in the chassis 2 in order to provide stability during stair climbing operations.

During stair climbing operations, the front of the vehicle, identified in FIG. 1B as the side in which the stereo-optic viewing port 9 is located, ordinarily is pointed up the stairs when the vehicle is powered to drive up the incline. At this time, payload 6, which is carried on articulated arm 5 and is connected to turret 4, ordinarily would be extended along the front sloping portion of cover 3 in order to further move the center of gravity as low and forward as possible, thereby providing additional stability to the vehicle. Optimally, for the vehicle sized as described herein, the center of gravity would be approximately 4 inches forward of center and 4 inches above the bottom of the chassis for stair ascent. By the same token, operation of the vehicle in a traverse along an incline slope can be made more stable by suspending the articulated arm over the up-slope side of the cover 3. The sloping face of the cover 3 when combined with the motion of the articulated arm and turret combination provides an additional measure of stability that reduces the need for other expensive stabilizing devices such as stabilizing arms or multiple tracks, as shown in the prior art. The turret and arm combination also provides stability to the vehicle during stair descending operations and, in particular, during the transition of the vehicle from a horizontal disposition to the stair incline such that the vehicle is prevented from tumbling forward over itself. In a maneuver to accomplish this result, the articulated arm is moved dynamically from a forward to a rearward position in order to provide stability as the vehicle transfers from a horizontal to the inclined position.

FIG. 5A illustrates the supervisory control station electronic subsystem which operates in a conventional manner but is specifically described with respect to conventional block elements. The command panel 501 is adapted to provide 15 or more different commands through previously described conventional controls 31 and 32 and to supply them to encoder 502 which provides an information stream in a conventional manner. Command control transmitter 503 modulates the encoded information onto a carrier which radiates signals through antenna 504 to the receive antenna on the vehicle.

Figure 5B:
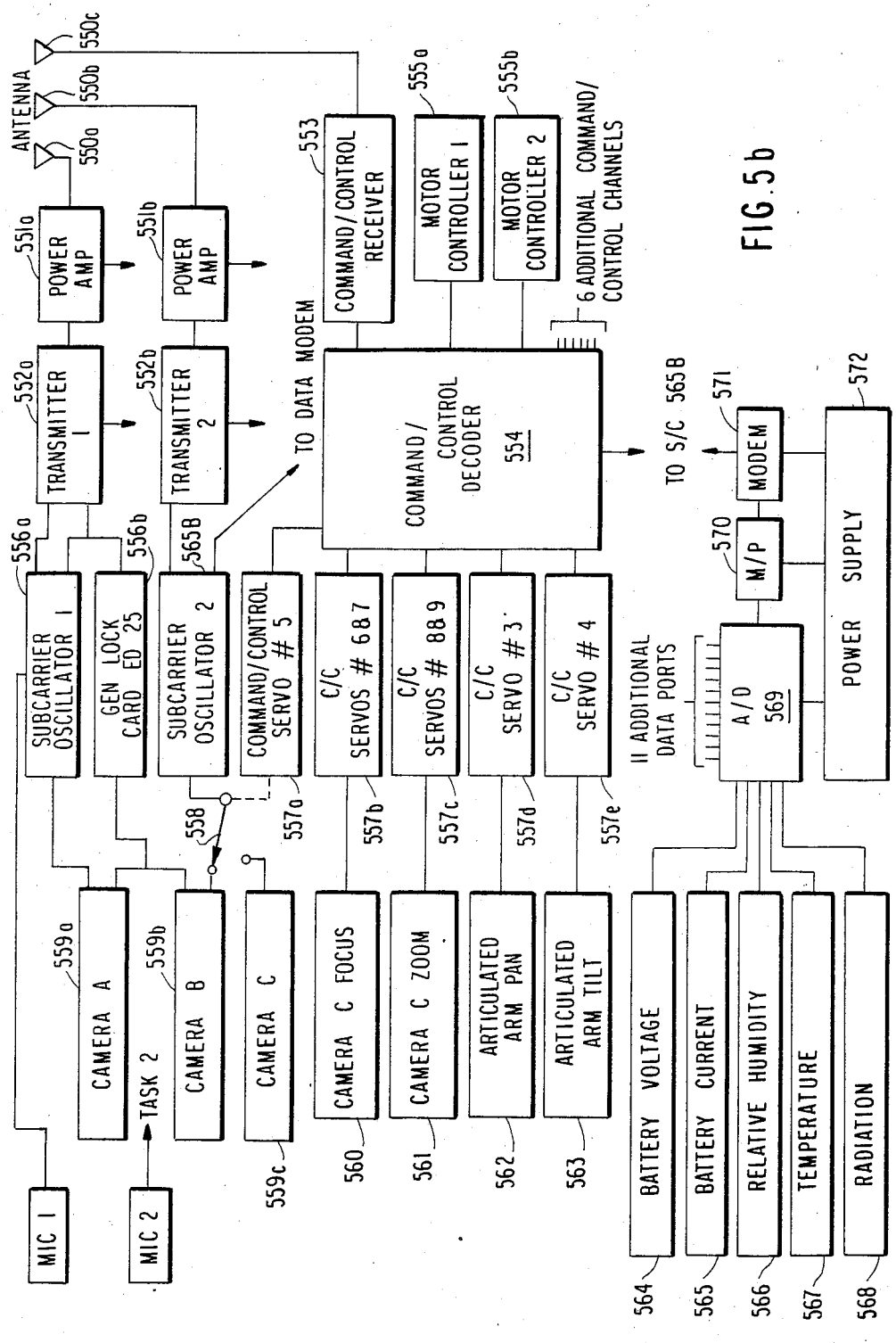
FIG. 5B is a block diagram of the remote control vehicle electronic subsystem.
Figure 5C:
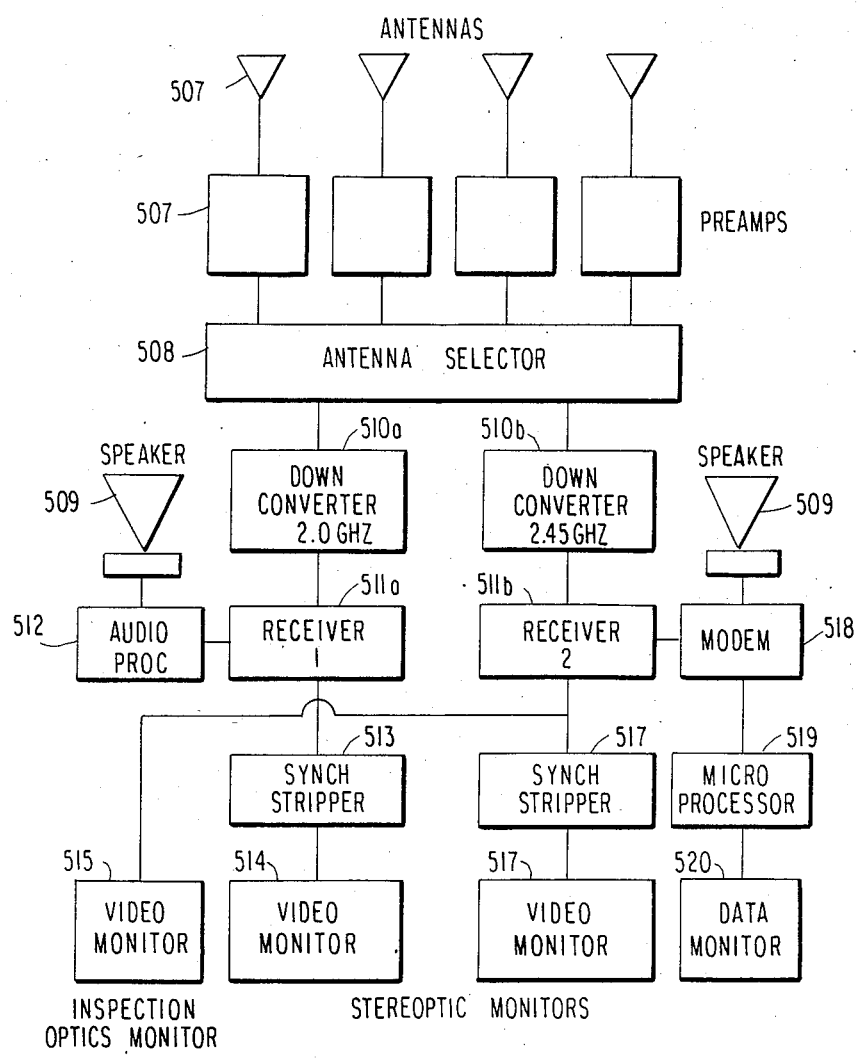

FIG. 5B illustrates the typical arrangement within the vehicle for controlling its operation. The encoded RF signal, is picked up by antenna 550c, is forwarded to command/control receiver 553 and is decoded in command control decoder 554 in a conventional manner. Appropriate control signals are transmitted to motor controllers 555a and 555b. Control and command servos 557 are operated in response to inputs from decoder 554 to provide proper power levels to a variety of related devices such as camera focus motor 560, camera zoom motor 551, articulated arm pan motor 562 and articulated arm tilt motor 563. Telemetry antenna 550a is connected to receive the input from microphone 1 and camera 559a, which are connected to subcarrier oscillator 556a, which in turn is connected to transmitter 552A and power amplifier 556a. In a similar fashion, the output from cameras 559b and 559c are switchable by servo control switch 558 to provide one or the other of cameras 559b or 559c to subcarrier oscillator 565b. The output of that oscillator is provided to transmitter 552b, whose output is boosted by power amplifier 551b and provided to antenna 550b. Telemetry is also provided from transducers 564, 565, 566, 567 and 568 to A/D converter 569. Additional data ports may be provided to the A/D converter as shown. The output of the converter is supplied to micro processor 570 whose output is supplied to modem 571 and then to subcarrier oscillator 565B. Power supply 572 is used to power the transmit and receive subsystem. All of the above functions are conventional in the prior art.

At the control station illustrated in FIG. 5a, antennas 507 receive the broadcast signals. After amplification by preamp 507, the output is provided to antenna selector 508 which selects the strongest of each pair of redundant signals. The strongest of the first pair is provided to down converter 510, which in turn supplies receiver 511a. The output of receiver 511a is provided to an audio processor 512 and speaker 509. Another output from receiver 511A is sent to a sync stripper 513 and video monitor 514 in a conventional manner. The other selected output channel is provided to down converter 510b operating at a different frequency. The output from the down converter 510B is provided to a second receiver 511b. The output from that receiver is supplied to video monitor 515 and sync stripper 516 which in turn supplies the output to video monitor 517 in a conventional manner. The output of receiver 511b also is provided to modem 518, which separates out the audio signal (for broadcast through speaker 509) from the data stream and provides the data stream to microprocessor 519 for analysis and display on data monitor 520. Video monitors 514 and 517, when viewed through the 3-D hood 33 of FIG. 3, provide the operator with a stereo-optic view from the remote control vehicle. Video monitor 515 provides the input from the inspection optic monitor 6 in FIG. 1A.

The maneuverability of the vehicle on a number of different surfaces, including the capability to climb stairs and to travel over obstacle and debris or other barriers is facilitated by the vehicle propulsion subsystem which includes the chassis, batteries, motors, gearboxes, drive wheels, road wheels, tracks, and track tensioners. The subsystem is sized for the tracks to span three stair risers on a conventional staircase having a 45° angle. Bow angle, stern angle and height of front top track idler are selected to provide optimum stair and obstacle climbing capability. A key to this capability is a low center of gravity, as previously discussed. However, the design of the treads and tread tensioner offers an additional capability for controlling the stability of the device.

FIGS. 6A and 6B illustrate an embodiment of the tread tensioner which is located external to the chassis and on its side, thereby permitting ready access for adjustment by an operator to adapt to various surfaces, and combines a tensioning mechanism with the front idler wheel 611. This unique design adapts to the natural stretch in the tread by incorporating a shock absorbing spring 620. Wheel 611 comprises two half wheels 611a and 611b, having a common shaft 612 and being supported by extendable arm 614, which is atttached to one end of shaft 615 which slides within bushing 616. Shaft 615 contains at the other end thereof a hollow portion 623 which contains the shock absorbing spring 620 and is prevented from passing through bushing 616 by met 624. Shaft 618 is aligned with its longitudinal axis coincident with the longitudinal axis of shaft 615 and is adapted to fit within the hollow portions of shaft 615 and abut the spring within that portion, whereby the spring can be compressed by pressure along the longitudinal axis. Shaft 615 acts through spring 620 against shaft 618, which is threaded to screw in and out of threaded hole 621 to position idler wheel 611 against the tread, thereby providing proper tread tension. The spring also 620 provides shock absorption. A lock nut 617 is adapted to hold the threaded shaft 611 in place, thereby maintaining a predetermined amount of pressure against the spring. Locknut 617 is loosened to allow tread tensioning by turning shaft 618 at 622. A constant pressure is thereby transmitted from the shaft to the wheel 611 and the spring is adapted to absorb any shock which may be developed when the tread impacts against an object. The entire mechanism is held by and attached to the vehicle by tensioner body 619.

Referring to FIG. 7A, a longitudinal and lateral cross-section of the tread is shown. The tread comprises a first belt 702 which is approximately ¼ inch thick and having raised ridges 703 of approximately ¼ height and spaced apart approximately ⅜ inches and sized to match with drive wheel 12, as shown in FIG. 1A. Another belt 704, which is bonded to belt 702 contains tread teeth 705 having a width, approximately 2 9/16 inches, being spaced apart by approximately 1¾ inches and a shape which is adapted to grip stair treads when climbing and to travel over most surfaces without being wedged therein, particularly metal grate surfaces commonly found in industrial facilities. The belts may be made of a flexible plastic or rubber material which preferably is not porous in order to minimize the effort for decontamination after a mission. FIG. 7B shows a transverse cross-section of the tread.

Figure 8A:
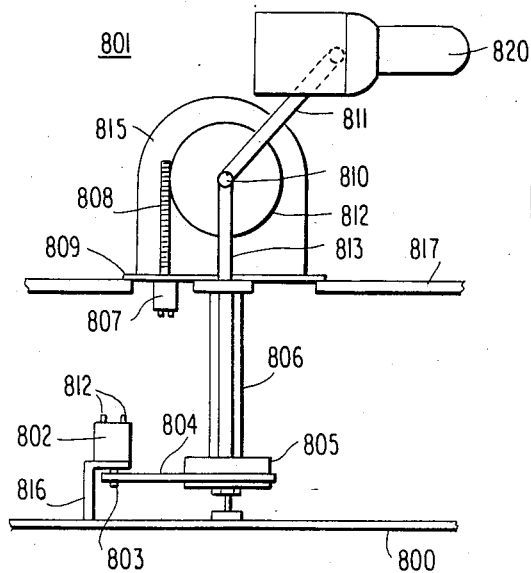
FIG. 8A illustrates one embodiment of an articulated arm payload.
Figure 8B:
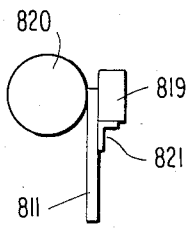
FIG. 8B illustrates a motor driven load for the arm payload.

Referring now to FIG. 8A, a preferred embodiment of a payload 801 for attachment to the horizontal deck 800 of the vehicle is shown. A motor 802 is attached by bracket 816 to the deck. The motor contains a gear 803 affixed to its drive shaft and is powered from terminals 812. A rotatable platform 809 located above the top cover 817, is affixed to rotating mounting post 806 which rides upon center post 818 affixed to deck 800, and has at a lower end a gear 805. Belt 804 is adapted to convert the rotation of gear 803 into rotation of mounting post 806 and thereby provide a panning capability in a 360° arc about the vertical axis passing through mounting post 806. Rotatable platform 809 also has mounted to it motor 807 having a worm gear 808. A bracket 813 is affixed to rotating platform 809 and is adapted to hold in a rotating fashion gear 812, which is attached to arm 811 and has shaft 810 passing centrally therethrough. Operation of motor 807 will turn worm gear 808 and, through its contact with gear 812, causing the arm 811 to rotate through an arc of 180°. The above top cover mechanism is encapsulated by a protective cover 815. As shown in FIG. 8B, an additional rotational capability is provided at the end of arm 811 with a load 820 having a motor 819, attached to arm 810 by bracket 821 and adaptable to be rotated by the motor shaft passing through the arm. The inspection optics 820 are thus mounted and are rotated in a ±180 degree arc by motor 819.

Additional loads which may be carried by the mechanism supported articulated arm 11 include a telescoping arm assembly which permits an extension of the arm to a distance of 15 feet. The telescoping assembly may carry a solid particle smear sampler and/or optical equipment or sensing equipment as has been taught by the preferred embodiment of this invention.

Figure 8C:
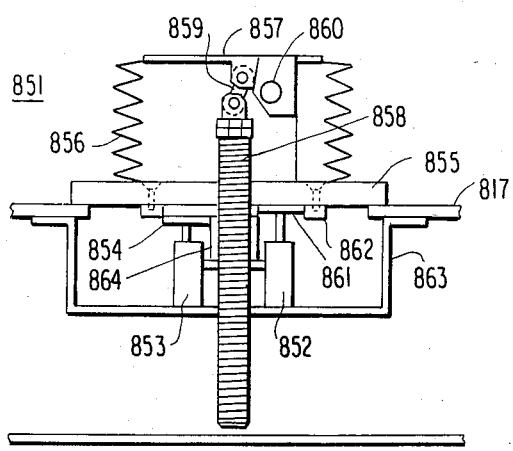
FIG. 8C illustrates a second embodiment of a rotational payload having a tilt mechanism.

FIG. 8C illustrates another embodiment of payload 851. This embodiment also provides pan and tilt motion but with a more compact configuration and with motors and mechanisms lower in the vehicle than the embodiment shown in FIG. 8A. The majority of mechanism 851 is below top cover 817 thus keeping the center of gravity low. A pan motor 852 drives a gear 861 which interfaces with internal ring gear 862 on turntable 855. Operation of the motor will cause the turntable 855 and all above deck parts of the mechanism to rotate with respect to the top surface 817. A tilt motor 853 drives a spurgear 854, which drives a drive hub 864, which drives screw drive mechanism 858 vertically up and down. The screw drive mechanism is attached to a flat surface 857 by a belt crank 859 that is connected to shaft 858. Operation of tilt motor 853 to move the shaft up or down will result in the mounting surface 857 being tilted about fulcrum 860. Stops are built into the shaft mechanism to limit the direction of travel. A cover 856 seals the drive mechanism and prevents contamination. All below cover parts are connected to mounting structure 863.

Figure 10:
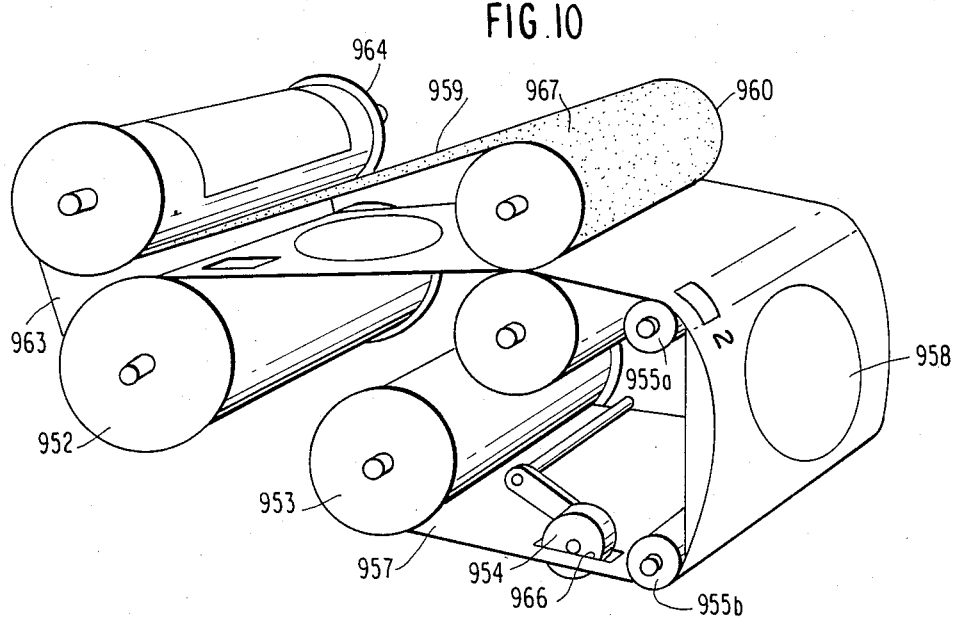
FIG. 10 illustrates the tape track system for a smear sampler.

A unique feature of this invention is its ability to automatically collect samples from the surface of the walls, floor or machinery within a contaminated environment. A unique smear sampler apparatus which is attached to the payload portion of the articulated arm, either directly by a mating connection 902 or through an extended arm segment 16, as shown in FIG. 1B, is contemplated. FIG. 9A illustrates a smear sampler drive mechanism which contains an adapter 902 for attaching the smear sampler to a payload articulated arm or its extension. The sampler holder 915 is connected to the arm interface by shaft 905 which is spring loaded against, and rides inside and follows cam slot 904a, thus forcing shaft 905 to rotate when pressure is applied along the longitudinal axis of shaft 905. When shaft 905 rotates so does the entire smear sampler holder and cassette assembly. This causes the smear sample patch 958 which is held against a cushioned collecting surface 956 and two roller guides 955a and 955b as seen in FIG. 9B, to rotate against the surface from which a sample is being taken. When pressure against shaft 905 is removed the shaft is spring driven to rotate back to its original position in a conventional manner. The holder 915 contains a motor 907 which drives the shaft 908 and worm gear 909 which drives gear 906. Gear 906 is connected to crown gear 910 which meshes with and directly drives crown gear 964 on the cassette as shown in FIG. 9B. Crown gear 964 is directly connected to sample takeup roller 952. The motor is driven by a battery 911 that is connected in a circuit with the motor by parallel, normally-open switches 912 and 913. Switch 912 is closed by remote command of the operator through a conventional solenoid or other mechanism. Once the motor begins to turn, switch 913 is closed by the movement of the tape across roller switch lever 954, that is mechanically connected to switch 913. In FIG. 9B, the base tape 957 is loaded into the cassette 951 on roller 953. Base tape 957, which contains sample patches 958, preferably at four inch intervals, is threaded over idler roller 955b, around sample patch backing pad 956, then back into the cassette over idler roller 955, between rollers 960 and idler 961, and onto sample base tape as it is threaded onto sample takeup roller 952. Referring to FIGS. 9A and 9B when motor 907 is actuated, the base tape 957 is collected by being rolled onto roller 952 and sample cover tape 954 is automatically applied to cover each sample pad 958 after a sample has been acquired. This assembly of base tape, sample patches and cover tape 962 is rolled onto sample takeup roller 952 and stored. The paper tape 963 which protects the adhesive side of cover tape 959 until it is ready for use is also automatically rolled onto sample takeup roller 952. FIG. 10 is a further illustration of FIG. 9B and shown in three dimensional perspective the action of the various rolls during the smear sampler operation. As can be seen in FIG. 10, the sample patch 958 is automatically positiond in sample-taking position by a spring loaded indexing roller lever 954 which drops into a slot 966 cut in the base tape. The roller level 954 is mechanically connected to normally open switch 913 in the holder 915 and the action of the spring loaded roller in dropping into slot 966 will cause switch 913 to open, thereby disconnecting power from motor 907. Motor 907 can be started again by the operator commanding switch 912 to close, which thereby moves the tape and causes the roller lever to rise out of slot 966 and close switch 913 which continues to operate until the next slot 966 is reached, at the proper position of the next sample pad 958. Again operation is automatically stopped by the indexing roller switch 954 when it drops into the slot in the base tape. As may be clear to one of ordinary skill in the art, the smear sampler may be adopted for a hand held operation by substituting a handle at interface 902 and placing in the handle, the battery 911 and switch 912, for manual operation by the operator. The sampler system will acquire up to 24 samples and protect them from cross contamination.

Figure 11A:
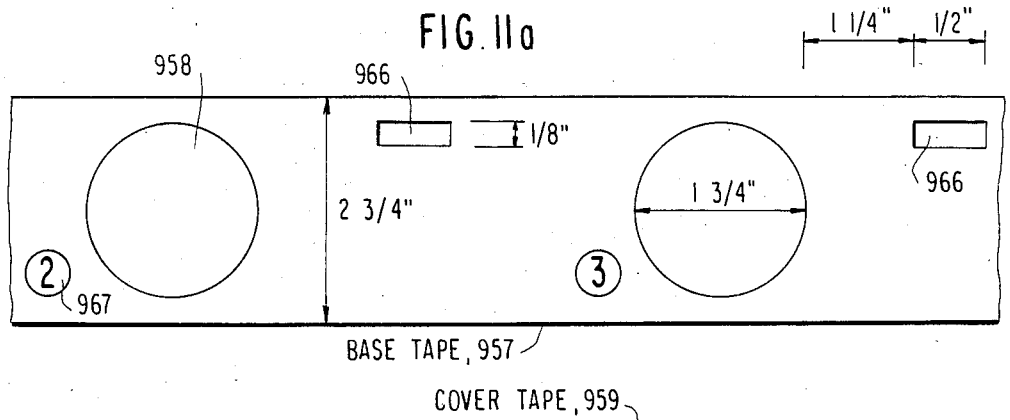
FIG. 11A illustrates the base tape design for the smear sampler.

FIG. 11A shows an illustration of a base tape 957 which typically is a mylar, polyester or paper tape, approximately 45 inches long and two and three-quarters inches wide. Affixed to the tape 957 is a number of cloth or paper samplers 958 spaced equally one from the other and centered between the sides of the tape. Each patch 958 is numbered in sequence 967. The base tape 957 contains an index hole 966 which is located in a position which causes roller switch 954 to drop, thereby cutting power to the drive motor, as explained above.

Figure 11B:
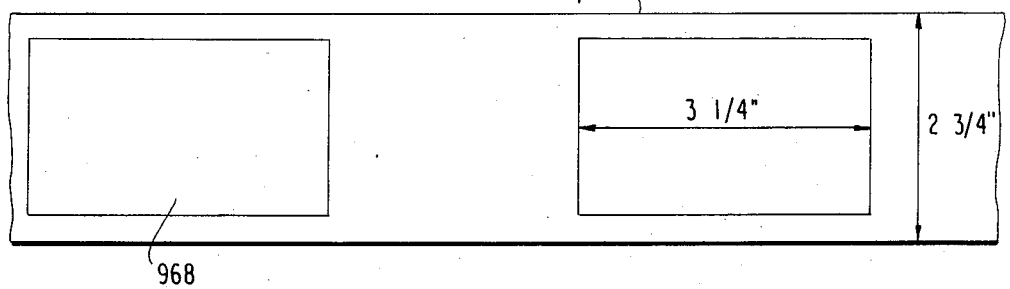
FIG. 11B illustrates the cover tape design for the smear sampler.

The cover tape 959, shown in FIG. 11B, is a mylar, polyester or similar material approximately the same length as the base tape 957 and is selectively printed with adhesive that will, when the tape is applied to the base tape 957, bond the two tapes together in areas other than the base tape sampler 958 and thereby isolate the paper or cloth samples from each other. The non-adhesive position of cover tape 959 is shown as 968 and is sized and oriented to cover and seal patches 958 on the base tape. In the case of each tape, it should be the thinnest, most flexible material possible so that the laminate of base tape and cover tape will roll as tightly as possible. The backside of the cover tape may be treated with silicon or other material so that when the tape is rolled, adhesive side in, the adhesive will not stick to the back of the tape. The base tape may have numbers printed on it for identification of the samples in the laboratory.

It should be understood, of course, that the foregoing disclosure relates only to a preferred embodiment of the invention and that it is intended to cover all changes and modifications which do not constitute departure from the spirit and scope of the invention.

I claim:

1. A remote control mobile surveillance system comprising:
   an operator control center, said center comprising manual command operation and transmission means, telemetry receive and reporting means and antenna means;
   a surveillance vehicle located remote from said control center and in wireless communication therewith, said vehicle comprising:
   chassis means, said chassis means being sized and shaped to fit within standard doorways and stairways and to provide an optimally low center of gravity for said vehicle;
   propulsion means adapted to provide movement to said vehicle and being mounted on said chassis means and comprising at least two independently controllable motor and track means;
   cover means removably mounted on said chassis means and adapted to support a plurality of payloads;
   payload means adapted to be movable in at least one direction and to have mounted thereon an operative load means, said payload means being removably mounted on said cover means;
   telecommunications means adapted to receive commands from and transmit telemetry to said operator control center, said means being operatively connected to said propulsion means and said payload means, whereby an operator at said operator control center can remotely control and monitor the movement of said vehicle and the operation of said payload means;
   said cover means being substantially rectangular in shape, having a vehicle front, a vehicle rear and two longitudinal side edges, a centrally located planar portion on which is mounted said payload means and a front planar apron portion extending from said payload at an angle downward to said vehicle front edge; and
   said payload means being adapted to move said operative load forward and below said centrally located planar position, along said planar apron position of said cover means, whereby the center of gravity of said vehicle may be moved lower and forward dynamically during movement of said vehicle up an inclined surface under remote control from said operator control center.

2. The remote control surveillance system claimed in claim 1 wherein said chassis means is an open top container having a substantially rectangular bottom portion, parallel side portions oriented orthogonal to said bottom portion and front and rear bow portions angled upward from said bottom portion at an angle within the range of 120°–140°, whereby said vehicle is better adapted to ascend and descend conventional stairways and to climb over barriers.

3. The remote control surveillance system claimed in claim 1 wherein said payload comprises an articulated arm means adapted to be movable in a pan and tilt direction.

4. The remote control surveillance system claimed in claim 3 wherein said articulated arm means has affixed thereto an operative load means which is adapted to take repetitive smear samples from surfaces within the range of motion of said arm means.

5. The remote control surveillance system claimed in claim 1 wherein said chassis includes a stereoptic viewing means, including two television cameras positioned to overlappingly view the forward direction of travel of said vehicle, said stereoptic viewing means being connected to said telecommunications means for transmission to said telemetry receive and reporting means whereby a three dimensional image of the vehicle foreground is provided to the operator.

6. A remote control surveillance vehicle responsive to an operator control center comprising:
   chassis means, said chassis means being sized and shaped to fit within standard doorways and stairways and to provide an optimally low center of gravity for said vehicle;

propulsion means adapted to provide movement to said vehicle and being mounted on said chassis means and comprising at least two independently controllable motor and track means;

cover means removably mounted on said chassis means and adapted to support a plurality of payloads;

payload means adapted to be movable in at least one direction and to have mounted thereon an operative load means, said payload means being removably mounted on said cover means;

telecommunications means adapted to receive commands from said operator control center and transmit telemetry to said operator control center, said means being operatively connected to said propulsion means and said payload means;

said cover means being substantially rectangular in shape, having a vehicle front, a vehicle rear and two longitudinal side edges, a centrally located planar portion on which is mounted said payload means and a front planar apron portion extending from said payload at an angle downward to said vehicle front edge; and wherein said payload means is adapted to move said operative load forward and below said centrally located planar position, along said planar apron position of said cover means, whereby the center of gravity of said vehicle may be moved lower and forward dynamically during movement of said vehicle up an inclined surface under remote control from said operator control center.

7. A remote control surveillance vehicle as claimed in claim 6 wherein said cover means further includes side planar apron portions extending along substantially the entire length of each longitudinal side edge and extending on each side from said centrally located planar position down to said longitudinal side edge;

wherein said payload means is adapted to move said operative load to the side of said vehicle and below said centrally located planar portion, whereby the center of gravity of said vehicle may be moved lower and to the side dynamically during movement of said vehicle in a traverse along an inclined surface.

8. A remote control surveillance vehicle as claimed in claim 6, wherein said chassis means is an open top container having a substantially rectangular bottom portion, parallel side portions oriented orthogonal to said bottom portion and front and rear bow portions angled upward from said bottom portion at an angle within the range of 120°–140°, whereby said vehicle is better adapted to ascend and descend conventional stairways and to climb over barriers.

9. A remote control surveillance vehicle as claimed in claim 8 wherein said chassis includes in said front bow portion a window means and is adapted to have mounted thereon in forward viewing relationships through said window a stereoptic viewing means comprising two television cameras positioned to overlappingly view the forward direction of travel of said vehicle and being connected to said telecommunications means for transmission of the television signals generated by said cameras.

10. A remote control surveillance vehicle as claimed in claim 8 wherein each of said motor and track means comprises a drive wheel rotatably mounted at the top of one of said parallel side portions of said chassis means;

a plurality of support wheels rotatably mounted along the bottom of one of said parallel side portion of said chassis means;

tensioner wheel means, said tensioner means comprising a rotatable idler wheel and an adjustable tension means mounted at the top of one of said parallel side portions of said chassis means, being spring-loaded and being adapted for manual adjustment of the spring tension; and a belt-like track, adapted to be wrapped around said drive wheel, said support wheels and said idler wheels and to be rotated by said drive wheel while being kept in tension by said tension wheel means.

11. A remote control surveillance vehicle as claimed in claim 10 wherein said belt-like track has tread means spaced apart and sized to enable stair and obstacle climbing while avoiding being wedged in standard industrial grated surfaces.

12. A remote control surveillance vehicle responsive to an operator control center comprising:

chassis means, said chassis means being sized and shaped to fit within standard doorways and stairways and to provide an optimally low center of gravity for said vehicle;

propulsion means adapted to provide movement to said vehicle and being mounted on said chassis means and comprising at least two independently controllable motor and track means;

cover means removably mounted on said chassis means and adapted to support a plurality of payloads;

payload means adapted to be movable in at least one direction and to have mounted thereon an operative load means, said payload means being removably mounted on said cover means;

telecommunications means adapted to receive commands from said operator control center and transmit telemetry to said operator control center, said means being operatively connected to said propulsion means and said payload means;

said payload means comprises pan motor means affixed to said cover means, said motor means including gear means and being rotatably operable;

turntable means adapted to be rotated by said pan motor means in a substantially horizontal plane;

tilt motor means, said means including gear means and being rotatably operable;

screw drive means mounted on said turn table means and being adapted to be driven in a substantially vertical up and down direction by operation of said tilt motor means;

mounting platform means; and bell crank means connected to said screw drive means and said mounting platform means and having a fulcrum means which is adapted to tilt said platform means as said screw drive means is driven up or down.

13. A remote control surveillance vehicle responsive to an operator control center comprising:

chassis means, said chassis means being sized and shaped to fit within standard doorways and stairways and to provide an optimally low center of gravity for said vehicle;

propulsion means adapted to provide movement to said vehicle and being mounted on said chassis means and comprising at least two independently controllable motor and track means;

cover means removably mounted on said chassis means and adapted to support a plurality of payloads;

payload means adapted to be movable in at least one direction and to have mounted thereon an operative load means, said payload means being removably mounted on said cover means;

telecommunications means adapted to receive commands from said operator control center and transmit telemetry to said operator control center, said means being operatively connected to said propulsion means and said payload means;

said operative load means includes a smear sampler mechanism, said mechanism comprising motor drive means for providing a rotational drive;

collecting surface means for placement against a contaminated surface; and tape means adapted to contain uncontaminated sample means and sample cover means for contamination, to pass said uncontaminated sample means over said collecting surface means, to mate said sample cover means with said contaminated sample means and to collect said mated cover and contaminated sample means.

14. A smear sampler mechanism comprising:

sampler cassette means for containing rolled sample base and cover tapes, said cassette means comprising a frame, a sample base tape roller rotatably mounted within said frame and adapted to carry a rolled base tape, a cover tape roller rotatably mounted within said frame and adapted to carry a rolled cover tape, a pressure pad means mounted external to said frame and being adapted to have said base tape pass from within said frame, across the surface of said pad means and back within said frame, a mating means adapted to receive said base tape after passing across said pad and said cover tape and to adhesively bond said cover tape to said base tape and tape collecting means rotatably mounted within said frame for rolling said bonded base and cover tapes; and sampler holder means, having a motor means and drive means connected to said motor means, said sampler holder means being adapted to receive said sampler cassette means and said drive means being adapted to rotatably contact said tape collecting means, thereby causing said types to be drawn from their respective rolls onto the tape collecting means.

* * * * *